(12) United States Patent
Guo et al.

(10) Patent No.: US 8,280,501 B2
(45) Date of Patent: Oct. 2, 2012

(54) SYSTEMS AND METHODS FOR QUANTITATIVELY CHARACTERIZING SLOW WAVE ACTIVITIES AND STATES IN SLEEP

(75) Inventors: Dan Guo, Beijing (CN); Yanhui Liu, Mountain View, CA (US)

(73) Assignee: Dyna Dx Corporation, Mountain View, CA (US)

( * ) Notice: Subject to any disclaimer, the term of this patent is extended or adjusted under 35 U.S.C. 154(b) by 368 days.

(21) Appl. No.: 12/761,712

(22) Filed: Apr. 16, 2010

(65) Prior Publication Data

US 2011/0257556 A1  Oct. 20, 2011

(51) Int. Cl.
*A61B 5/04* (2006.01)
(52) U.S. Cl. ...................................................... 600/544
(58) Field of Classification Search .................. 600/544, 600/545
See application file for complete search history.

(56) References Cited

U.S. PATENT DOCUMENTS

| | | | |
|---|---|---|---|
| 6,157,857 A | 12/2000 | Dimpfel | |
| 6,272,378 B1 | 8/2001 | Baumgart-Schmitt | |
| 6,381,559 B1* | 4/2002 | Huang | 702/194 |
| 2006/0293608 A1* | 12/2006 | Rothman et al. | 600/545 |
| 2008/0021345 A1* | 1/2008 | Kern et al. | 600/554 |
| 2009/0192556 A1* | 7/2009 | Wu et al. | 607/3 |
| 2010/0109881 A1* | 5/2010 | Eskandarian et al. | 340/575 |

* cited by examiner

*Primary Examiner* — Navin Natnithithadha
*Assistant Examiner* — Etsub Berhanu
(74) *Attorney, Agent, or Firm* — SV Patent Service (57) ABSTRACT

A method for quantitative sleep characterization includes acquiring a surface electroencephologram (surf-EEG) signal from an individual by a probe, decomposing the surf-EEG signal into a plurality of intrinsic mode functions (IMFs) by a computer processor in communication with the probe, wherein the plurality of IMFs comprises a first group of IMFs and a second group of IMFs, calculating a ratio comprising an amplitude or power of at least one of the IMFs in the first group in the numerator and a corresponding amplitude or power of at least one of the IMFs in the second group in the denominator; and identifying a period in the surf-EEG waveform as slow wave sleep (SWS) if the ratio associated with the period is above a predetermined threshold.

20 Claims, 11 Drawing Sheets

SYSTEMS AND METHODS FOR QUANTITATIVELY CHARACTERIZING SLOW WAVE ACTIVITIES AND STATES IN SLEEP

BACKGROUND

Objective and quantitative evaluation of sleep quality is an important issue in medicine. It is known that wake and sleep can be distinguished using surface electroencephalogram (surf-EEG) recording. A deep sleep state can be visually recognized in surf-EEG recording by its slow wave activities (SWA). The deep sleep state is thus called slow wave sleep (SWS). SWS is an important sleep state for re-storage and recovery of our body and brain. During SWS, people are not easy to be woken up compared to other sleep states, and have stronger vagal tone, relatively low and stable cardiopulmonary activity.

Since 1960s, the evaluation of sleep states involves manual SWS scoring by doctors and special technicians. With a series of rules, sleep is divided into rapid eye movement (REM) sleep and non-REM (NREM) sleep. The latter is further divided into NREM 1, 2, 3 sleep, wherein NREM 3 is the so-called SWS. The visual scoring standards of SWS include (1) 0.5 Hz - 4 Hz SWA; (2) the amplitude of each slow wave more than 75 μv; (3) SWA occupying more than 20% of a 30-second epoch.

A major drawback of the conventional sleep evaluation techniques is that the visual scoring can often produce large differences among individual scorers. Moreover, conventional techniques rarely find SWS in the old age group despite that SWA-rebound has been demonstrated to exist in the old age group after sleep deprivation. The research results show that the rebound proportion and decay slope in the old age group nearly identical with those in the young age group. It is suggested that the inability to identify SWS in the old age group is caused by the arbitrary definitions of amplitude and percentage in the conventional sleep evaluation techniques.

Although attempts have been made to quantitatively evaluate sleep physiology using the intensity of SWA, an objective index for SWA quantification has yet to be established in clinic and research. Different laboratories presently choose different temporary methods to quantify sleep quality for individuals with Fast Fourier transform the most widely used analytical algorithm. These techniques are challenged by the large variety of SWA generation and synchronization in human brains, the differences in skull impedance between individuals, and noise and other signal contamination in the EEG signals.

SUMMARY

The systems and methods described in the present application attempt to overcome the above described difficulties in the conventional techniques, and to provide an objective, quantitative, more accurate, and more reliable evaluation of sleep. The presently disclosed systems and methods can quantify SWA and determine sleep states for all age groups. Unlike Fast Fourier transform used in the conventional techniques, the presently disclosed systems and methods use nonlinear dynamics analysis and SWA to quantify sleep quality. The disclosed methods can further demonstrate that NREM sleep can be characterized by a bimodal rather than a multi-state process as defined in conventional sleep criteria.

The disclosed methods are non-invasive, can be fully automated, and can enable accurate diagnosis of a wide range of pathological conditions. The described systems and methods are also simpler and less expensive than some conventional techniques.

In a general aspect, the present invention relates to method for quantitative sleep characterization, comprising: acquiring a surface electroencephalogram (surf-EEG) signal from an individual by a probe; decomposing the surf-EEG signal into a plurality of intrinsic mode functions (IMFs) by a computer processor in communication with the probe, wherein the plurality of IMFs comprises a first group of IMFs and a second group of IMFs; calculating a ratio comprising an amplitude of at least one of the IMFs in the first group in the numerator and an amplitude of at least one of the IMFs in the second group in the denominator; and identifying a period in the surf-EEG waveform as slow wave sleep (SWS) if the ratio associated with the period is above a first predetermined threshold.

Implementations of the system may include one or more of the following. The step of decomposing the surf-EEG signal can be conducted using ensemble empirical mode decomposition. The first group of IMFs can have characteristic fluctuations in a frequency range from approximately 0.3 Hz to approximately 4 Hz, wherein the second group of IMFs have characteristic fluctuations in a frequency range below approximately 0.3 Hz. The second group of IMFs can have characteristic fluctuations in a frequency range from approximately 0.01 Hz to approximately 0.2 Hz. The first group of IMFs can have higher fluctuation frequencies than the second group of IMFs. The method can further include calculating a first average amplitude of at least one of the IMFs in the first group within a moving window; and calculating a second average of at least one of the IMFs in the second group within the moving window, wherein the numerator of the ratio comprises the first average amplitude and the denominator of the ratio can include the second average amplitude. The method can further include summing the first average amplitudes of the IMFs in the first group within the moving window to produce a first combined average amplitude; and summing the second average amplitudes of the IMFs in the second group within the moving window to produce a second combined average amplitude, wherein the step of calculating a ratio comprises calculating a ratio of the first combined average amplitude to the second combined average amplitude. The method can further include normalizing the first average amplitude of the at least one of the IMFs in the first group within the moving window; and normalizing the second average amplitudes of the IMFs in the second group within the moving window, wherein the step of calculating a ratio can include calculating a ratio of the normalized first combined average amplitude to the normalized second combined average amplitude. The method can further include normalizing the first average amplitudes of the IMFs in the first group within the moving window, wherein a period in the surf-EEG waveform is identified as slow wave sleep if the ratio associated with the period is above the first predetermined threshold and the normalized first combined average amplitude is above a second predetermined threshold.

In another general aspect, the present invention relates to a method for quantitative sleep characterization. The method includes acquiring a surface electroencephalogram waveform from an individual by a probe; decomposing the surf-EEG signal into a plurality of intrinsic mode functions by a computer processor in communication with the probe, wherein the plurality of IMFs comprises a first group of IMFs and a second group of IMFs; calculating a ratio comprising a power of at least one of the IMFs in the first group in the numerator and a power of at least one of the IMFs in the second group in the denominator, wherein the power of an IMF is proportional to the square of the amplitude or intensity of the IMF; and identifying a period in the surf-EEG waveform as slow wave sleep if the ratio associated with the period is above a predetermined threshold.

In another general aspect, the present invention relates to a method for quantitative sleep characterization. The method includes acquiring a surface electroencephalogram signal from an individual by a probe; decomposing the surf-EEG signal into a plurality of intrinsic mode functions by a computer processor in communication with the probe; comparing, by the computer processor, an amplitude of at least one of the IMFs to an amplitude threshold (At) at a plurality of sampling points in a moving window; determining the number of sampling points in the moving window that have the amplitude of the least one of the IMFs above At; and identifying the moving window as slow wave sleep if the number of sampling points having associated amplitudes above At is above an incidence threshold (Int) in the moving window.

Implementations of the system may include one or more of the following. The method can further include adding the amplitudes of a group of IMFs in the plurality of IMFs to produce a combined amplitude at the plurality sampling points, wherein the step of comparing comprises comparing the combined amplitude to At at the plurality sampling points, wherein the step of determining the number of sampling points comprises determining the number of sampling points in the moving window that have the combined amplitude above At, wherein the moving window is identified as SWS if the number of sampling points having associated combined amplitudes above At is above Int in the moving window. The method can further include computing one or more SWS percentages in the surf-EEG signal using the number of moving windows identified as SWS; calculating the SWS percentage as a function of Int; determining a plateau region in the function that has gradient below a predetermined value; and determining a stable percentage value associated with the plateau region in the function to characterize the portion of SWS in the surf-EEG signal.

In another general aspect, the present invention relates to a computer program product comprising a computer useable medium having computer readable program code functions embedded in said medium for causing a computer to: receive a surface electroencephalogram signal acquired by a probe from an individual; decompose the surf-EEG signal into a plurality of intrinsic mode functions that comprise a first group of IMFs and a second group of IMFs; calculate a ratio comprising an amplitude or a power of at least one of the IMFs in the first group in the numerator and a corresponding amplitude or power of at least one of the IMFs in the second group in the denominator; and identify a period in the surf-EEG waveform as slow wave sleep if the ratio associated with the period is above a predetermined threshold.

In another general aspect, the present invention relates to a system for quantitative sleep characterization. The system includes a first probe configured to acquire a surface electroencephalogram signal from an individual by a probe; and a computer processor in communication with the probe. The computer processor can decompose the surf-EEG signal into a plurality of intrinsic mode functions that comprise a first group of IMFs and a second group of IMFs, to calculate a ratio comprising an amplitude or a power of at least one of the IMFs in the first group in the numerator and a corresponding amplitude or power of at least one of the IMFs in the second group in the denominator, and to identify a period in the surf-EEG waveform as slow wave sleep if the ratio associated with the period is above a predetermined threshold.

Although the invention has been particularly shown and described with reference to multiple embodiments, it will be understood by persons skilled in the relevant art that various changes in form and details can be made therein without departing from the spirit and scope of the invention.

BRIEF DESCRIPTION OF THE DRAWINGS

The following drawings, which are incorporated in and form a part of the specification, illustrate embodiments of the present invention and, together with the description, serve to explain the principles of the invention.

DETAILED DESCRIPTION

Figure 1:
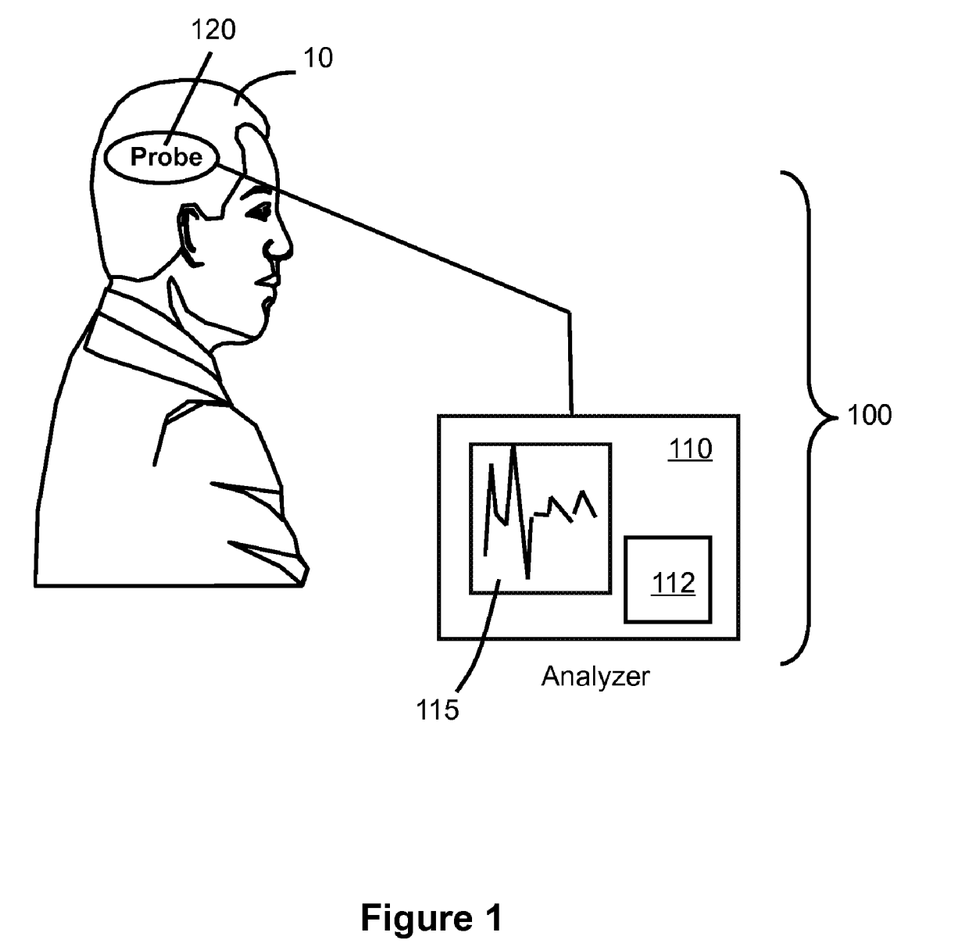
FIG. 1 is a schematic diagram illustrating a system for evaluating sleep in accordance to the present invention.

Referring to FIG. 1, an exemplified sleep evaluation system 100 includes an analyzer 110 and a probe 120 that can be attached to a patient 10. The probe 120 can include sensors and/or transducers configured to measure physiological signals such as electroencephalogram (surf-EEG) signal from the patient 10. The probe 120 can send sensing signals to the analyzer 110 in response to the physiological signals. The sensing signals are often in analog form. The analyzer 110 can include an analog-to-digital (A/D) converter for digitizing the sensing signals. The analyzer 110 also includes a computer processor 112 that is configured to process and analyze the sensing signals after they are digitized by the A/D converter. An algorithm can be pre-stored in a computer memory in the analyzer 110 for analyzing the sensing signals. The analyzer 110 can also include necessary input/output devices that allow a user to enter instructions to process the data, and a display 115 for displaying the raw sensing signals and data calculated from the sensing signals.

Figure 2:
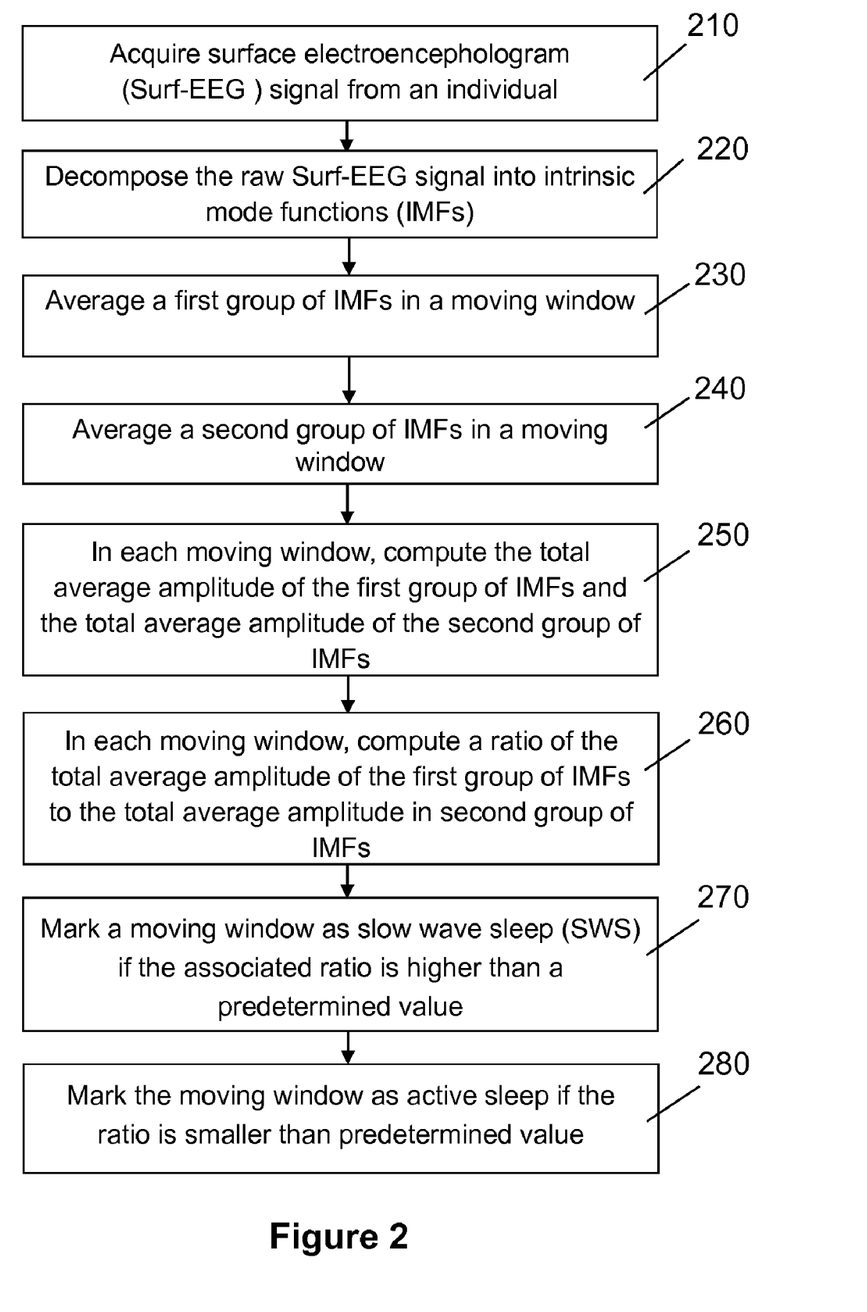
FIG. 2 is an exemplified flow diagram illustrating the steps of quantitatively evaluating sleep in accordance to an aspect of the present invention.

In some embodiments, referring to FIG. 2, a surf-EEG signal is recorded from the individual 10 using the sleep evaluation system 100. The surf-EEG data may be acquired from the individual 10 during a whole night of sleep (step 210). A 15 second period of surf-EEG data acquired at a 128 Hz sampling rate is shown in FIG. 3.

Figure 3:
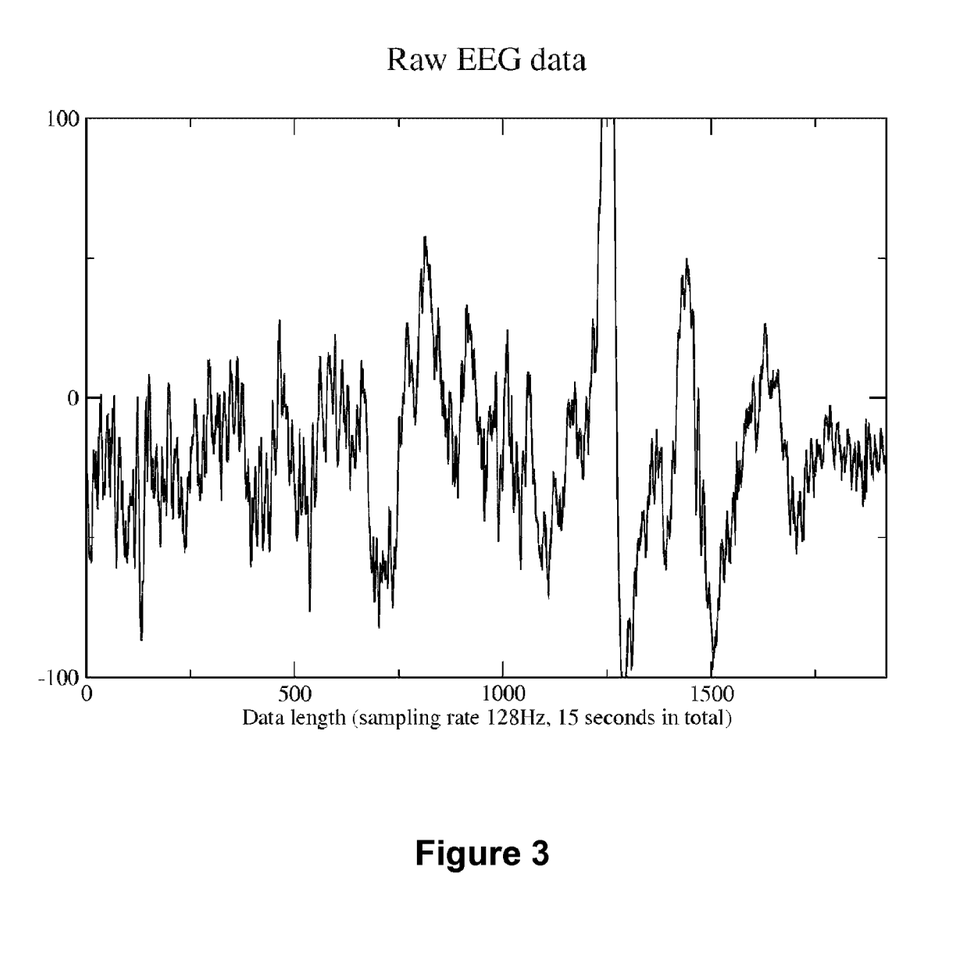
FIG. 3 illustrates a waveform of unprocessed signal obtained from surface electroencephalogram (sur-EEG) recording.

The surf-EEG waveform as shown in FIG. 3 is not stationary. In other words, the amplitudes (or powers) and frequencies of the surf-EEG waveform vary over time. Conventional Fourier transforms, however, cannot accurately describe non-stationary signals because these signals are non-periodic. In the present disclosed methods and systems, physiological sleep signals such as surf-EEG are analyzed as non-stationary oscillations. The amplitudes (or powers) and phases (or frequency) are characterized at any instantaneous moment. The surf-EEG data (amplitude or power) is decomposed into intrinsic mode functions (IMFs) (step 220) using ensemble empirical mode decomposition (EEMD) technique (which is also called Hilbert Huang transform). Each IMF represents a frequency-amplitude modulation in a narrow band that can be related to specific sleep process.

EEMD functions like filters to extract frequency components from non-stationary signals with varying amplitudes (or powers), phases, and frequencies. The IMFs has decreasing oscillation frequencies from low IMFs (e.g. IMF 1) to high IMFs (IMF 10). In one implementation, Mode 1 (or IMF 1) is obtained by tracing the envelope of local maxima and local minima in the surf-EEG waveform. Mode 1 is then subtracted from the surf-EEG waveform to obtain a first residual signal. Mode 2 (or IMF 2) is obtained by tracing the envelope of the maxima and minima in the first residual signal. Mode 2 is then subtracted from the first residual signal to obtain a second residual signal. Mode 3 (or IMF 3) is similarly calculated from the second residual signal. The above described decomposition steps are repeated to compute Mode 4 (or IMF 4) to Mode 12 (or IMF 12) of the IMFs for surf-EEG waveform. Such decomposition algorithm generally results in decreased oscillation frequencies from Mode 1 to Mode 12 in the intrinsic mode functions. The oscillation frequencies of the successive IMFs approximately decrease by a factor of two. The IMFs are usually characterized by frequency-amplitude modulation in a narrow frequency band. Physiological or pathological processes can be associated with certain specific frequency ranges.

Figure 4A:
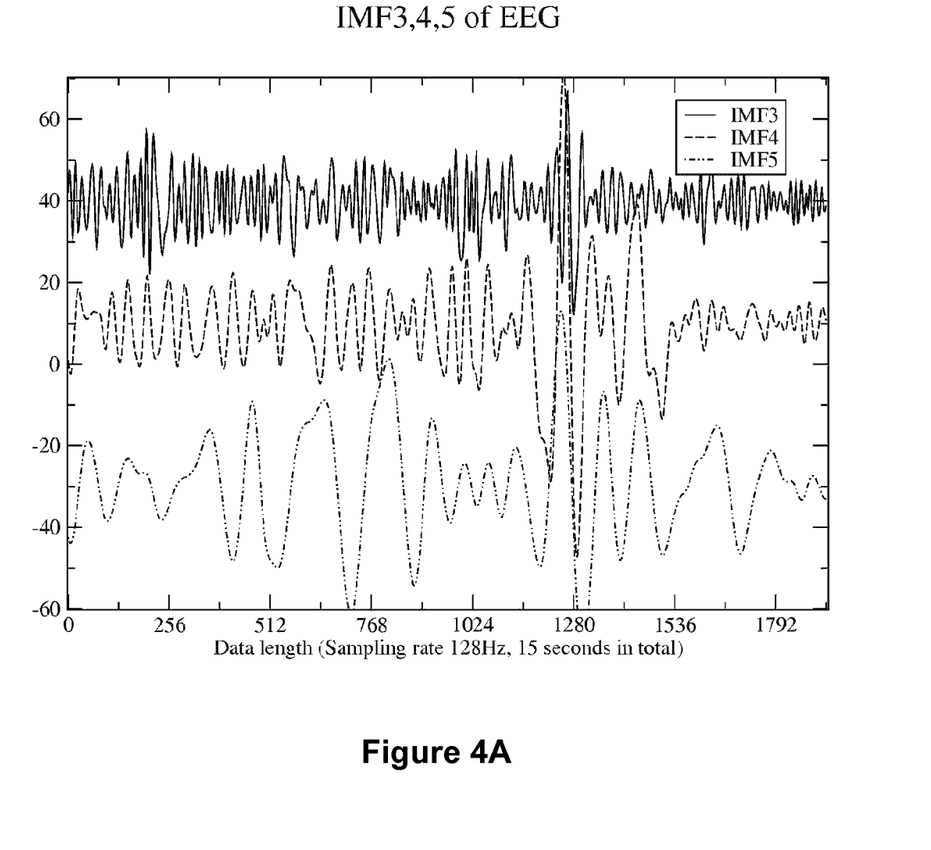
FIG. 4A illustrates waveforms of the first group of intrinsic mode functions (IMF) obtained from decomposing the raw sur-EEG data shown in FIG. 3.
Figure 4B:
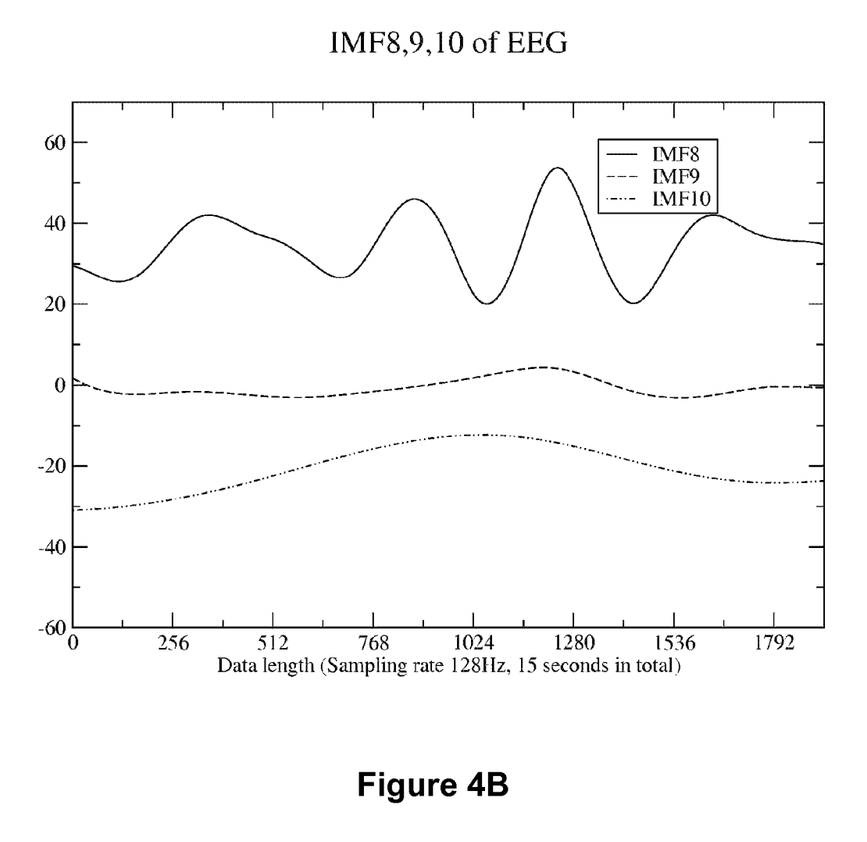
FIG. 4B illustrates waveforms of the second group of intrinsic mode functions (IMF) obtained from decomposing the raw sur-EEG data shown in FIG. 3.

FIGS. 4A and 4B respectively show the waveforms of IMFs 3, 4, 5 and IMFs 8, 9, 10 obtained from EEMD. The two groups of IMF waveforms are obviously different. The rhythm fluctuations of the two groups of IMFs are in different frequencies. The waveforms IMF 3, 4, 5 has an approximate frequency range from 0.3 Hz to 4 Hz, while the waveforms IMF 8, 9, 10 has a lower approximate frequency range below 0.2 Hz. The waveforms of IMF 3, 4, 5 have variation frequencies related to slow wave activities which are the characteristics of SWS. In the present exemplified application, IMFs 3, 4, 5 can also be called "SWA-related IMFs". IMFs 8, 9, 10 have lower frequency variations and can be called as "Infra-slow IMFs". The other IMFs (e.g. 1, 2) could be ignored at the present signal sampling frequency when these modes have their range of frequency variations that reveal little correlation with slow wave activity.

Figure 5A:
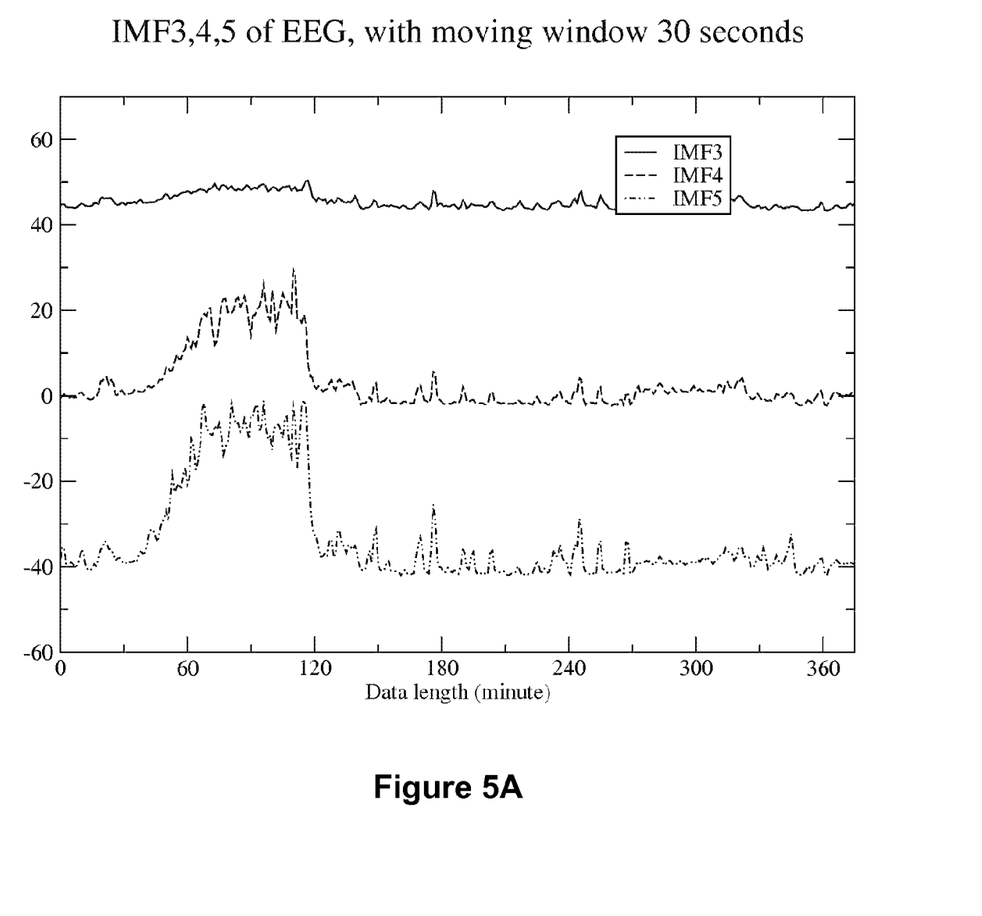
FIG. 5A illustrates waveforms of the first group of IMFs averaged with a 30 second moving window.
Figure 5B:
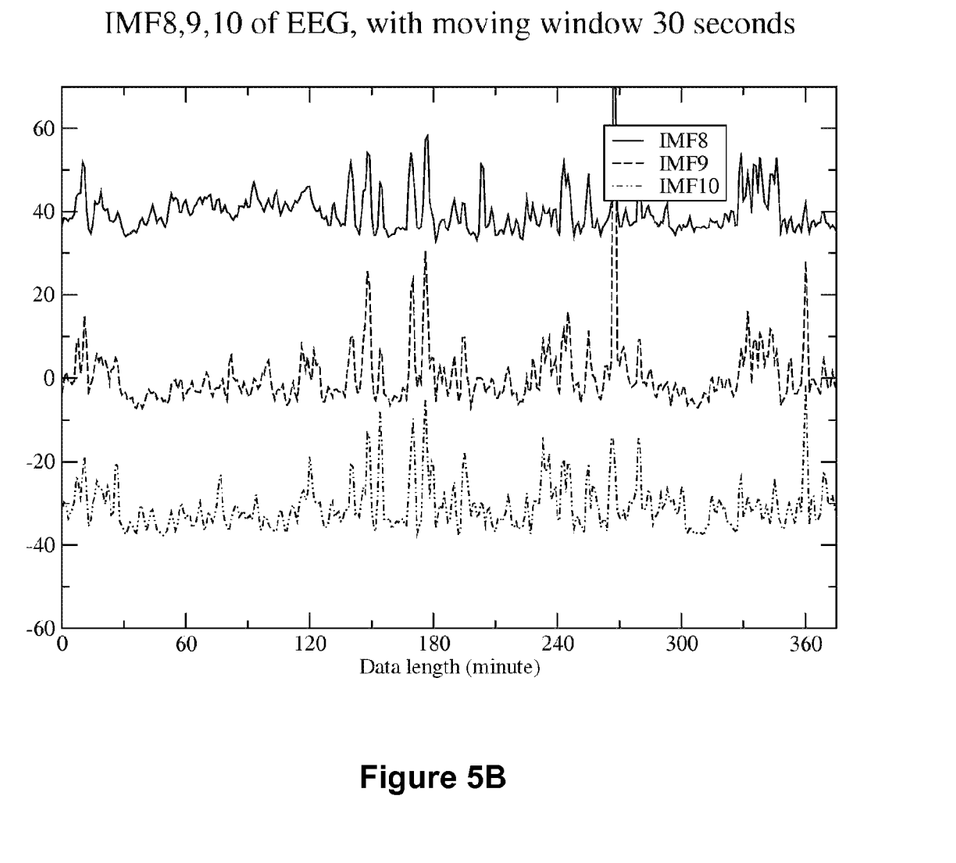
FIG. 5B illustrates waveforms of the second group of IMFs averaged with a 30 second moving window.

In addition, it is discovered that the amplitudes (i.e. the intensities) or powers of the two groups of IMF waveforms also appear to have different patterns of variations over time. The oscillation amplitudes (or powers) for the two groups of IMFs can be extracted from the complex EEG rhythm fluctuations to characterize SWA in the individual's sleep. The amplitudes of the first group of IMFs 3, 4, 5 are averaged in moving 30 second windows to produce smoother waveforms, as shown in FIG. 5A (step 230). The amplitudes of the first group of IMFs 8, 9, 10 are averaged in moving 30 second windows to produce smoother waveforms, as shown in FIG. 5B (step 240). (It should be noted that the time duration in FIG. 5B is more than 360 minutes while the waveform in FIG. 4B is sampled in 15 seconds.)

Figure 5C:
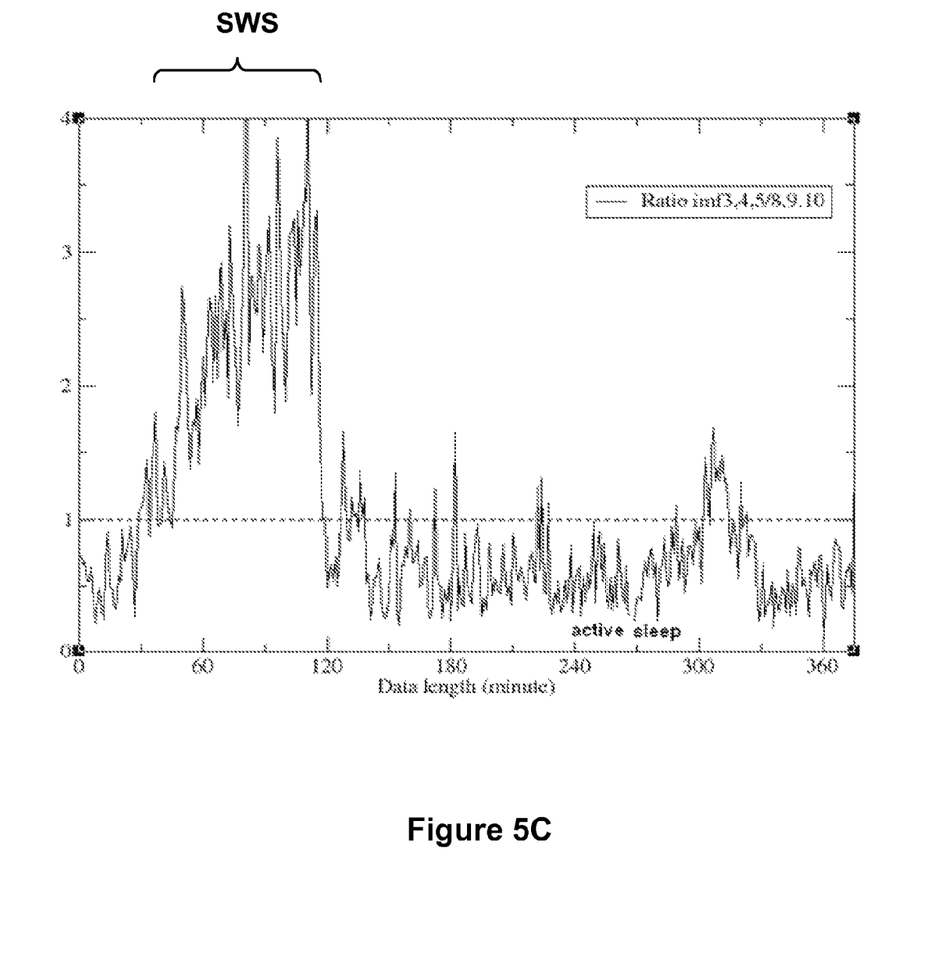
FIG. 5C shows the ratio of the combined average amplitudes (FIG. 5A) of the first group of IMFs over the combined average amplitudes (FIG. 5B) of the second group of IMFs.

Next, the average amplitude of the IMF 3, IMF 4, and IMF 5 in the first group and the average amplitude of the IMF 8, IMF 9, and IMF 10 in the second group are respectively summed within each moving window (step 250). In each moving window, the amplitudes of the IMF 3, IMF 4, and IMF 5 are added; so are the amplitudes of the IMF 8, IMF 9, and IMF 10. For each moving window, the ratio of the combined average amplitude of the first group of the IMFs (such as 3, 4, 5) to the combined average amplitude of the second group of the IMFs (such as 8, 9, 10), as shown in FIG. 5C, is calculated (step 260).

It the present disclosure, the term "average" refers to average of amplitude of a single IMF within a moving window; the term "total" refers to the summation of average amplitudes of different IMFs of a same group within a moving window.

In the present disclosure, such ratio is used to quantitatively characterize the sleep states of the individual. A high ratio value indicates that slow wave activities in the 0.3 Hz to 4 Hz range dominate the surf-EEG, which is thus a kind of representation of the SWS. A low ratio value indicates that higher frequency variations (usually >4 Hz) dominate the surf-EEG data, which is thus a better representation of the active sleep. As shown in FIG. 5C, when the ratio in a moving window is more than a predetermined threshold, this period of sleep in the moving window is classified as SWS, or inactive sleep or deep sleep (step 270). When the ratio within a moving window is less than or equal to the predetermined threshold, the period classified as active sleep (step 280). The predetermined threshold can for example be 1. In other words, the crossover at the threshold by the amplitude ratio between low IMF modes to the high IMF modes can be used as a "biomarker" for indicating SWS.

It should be noted that instead of using amplitudes, power, that is, the square of the amplitude, can be used in steps 230 to 280. In steps 230 and 240, the powers of the IMFs in the first group and the second group can be respectfully averaged. In step 250, the powers of the IMFs in each of the first and the second groups are summed. In step 260, the ratio of the total average power of the first group to the second group is computed. The power ratio is used in steps 270 and 280 to quantify SWS and active sleep phase.

An advantage of the presently disclosed methods is that they can quantitatively characterize sleep state for all age groups, which is a significant improvement over conventional techniques that fail to identify SWS in old age group. Furthermore, the disclosed methods can characterize sleep states in a bimodal fashion: a sleep period is either SWS or not, which is a simplification from the multi-state characterization in some conventional techniques. An important aspect of the disclose sleep characterization technique is that it is based on non-linear dynamics analysis instead of a linear analytical transformation (e.g. Fourier transforms). It is noted that the above described methods can most conveniently applied to surf-EEG data that give rise to comparable magnitudes in the combined average amplitudes between the two group of IMFs.

Figure 6:
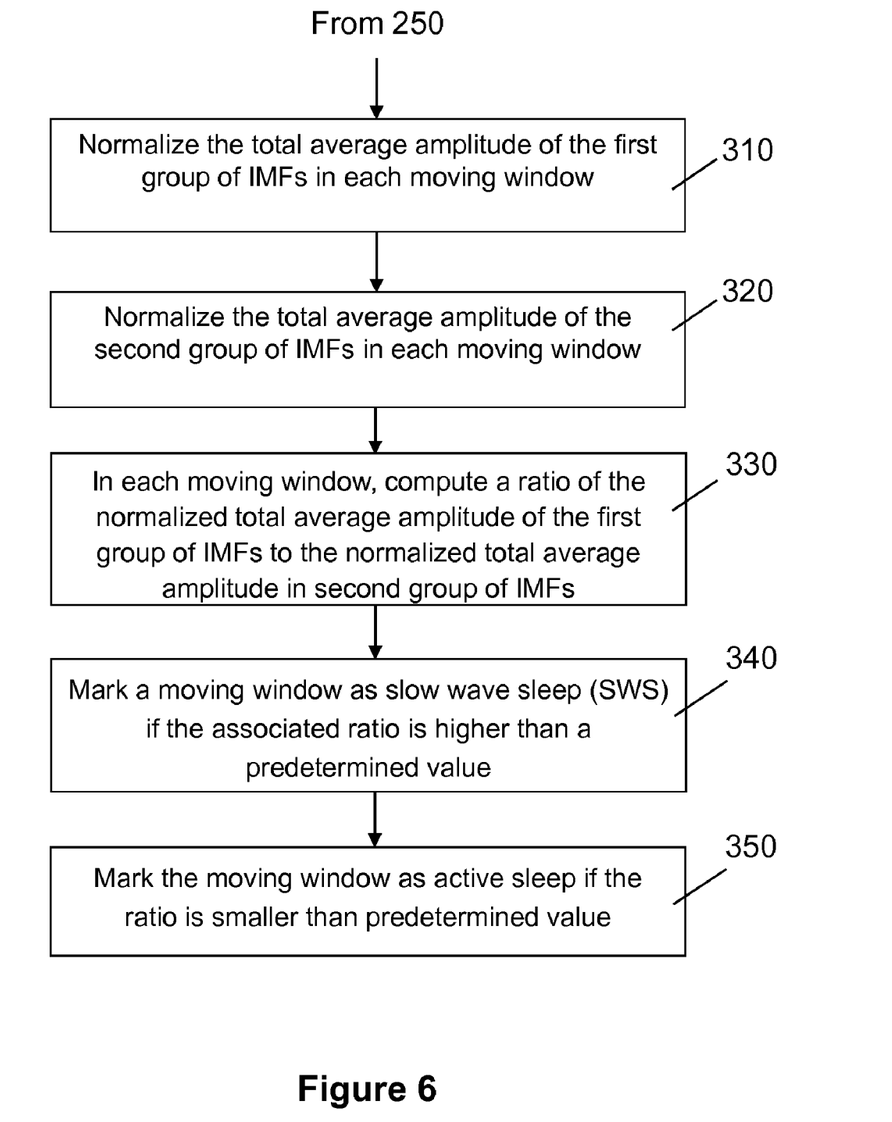
FIG. 6 is an exemplified flow diagram illustrating the steps of quantitatively evaluating sleep in accordance to another aspect of the present invention.

In some embodiments, the two groups of IMFs have different magnitudes in the average amplitudes (or powers). For example, the IMFs 3, 4, 5 may have higher average amplitude than the average amplitude of the IMFs 8, 9, 10 because the hardware setting during data collection has filtered out the signals below 0.5 Hz. Several steps can be added and modified relative to the process shown in FIG. 2 when the average amplitudes of the two IMF groups are rather different. Referring to FIG. 6, after step 250 (FIG. 2), the average amplitude of the first group of IMFs 3, 4, 5 is normalized to result in a normalized amplitude in each moving window (step 310). The normalization can be conducted by dividing the sum of the average amplitudes of the IMFs 3, 4, 5 in different moving windows by a predetermined percentage of the maximum value of the combined average amplitude. For example, the predetermined percentage value can be 55%, 60%, etc. Similarly, the combined average amplitude of the second group of IMFs 8, 9, 10 is normalized to produce a normalized amplitude in each moving window (step 320).

Similar to step 260 (FIG. 2), the ratio between the normalized combined average amplitude of the first group of IMFs (e.g. 3, 4, 5) to the normalized combined average amplitude of the second group of IMFs (e.g. 8, 9, 10) in each moving window, is calculated (step 330). Similar to step 270 (FIG. 2), when the ratio in a moving window is more than a predetermined threshold, this period of sleep in the moving window is classified as SWS (step 340), or inactive sleep or deep sleep. When the ratio within a moving window is less than or equal to the predetermined threshold, the period classified as active sleep (step 350). The predetermined threshold can for example be 1. It should be noted that, similar to the steps shown in FIGS. 2 and 3, powers instead of amplitudes can be used in steps 310 to 350.

In some embodiments, the criteria for sleep characterization can include a combination of the ratio of the normalized combined average amplitudes of the two groups of IMFs and the normalized combined average amplitude of the low IMFs. Since the combined average amplitude of the IMFs 3, 4, 5 is normalized by 55%-65% of the maximum value of the combined average amplitude, the normalized combined average amplitudes in the first group of the IMFs 3, 4, 5 should vary below 1 in certain periods to above 1 in other periods. In accordance to the present application, a moving window can be characterized as SWS when the previously described normalized ratio is more than the predetermined threshold (e.g. 1) and the normalized combined average amplitude of the IMFs 3, 4, 5 is more than 1.

The determination of SWS state in a surf-EEG signal can be sensitive to the threshold chosen for the amplitude of the low IMFs, as well as sensitive to the sampling frequency. The presently disclosed systems and methods provides a SWS identification approach that is insensitive to the selection of IMF amplitude threshold and the temporary dips of the low IMF intensities during a SWS state.

Figure 7:
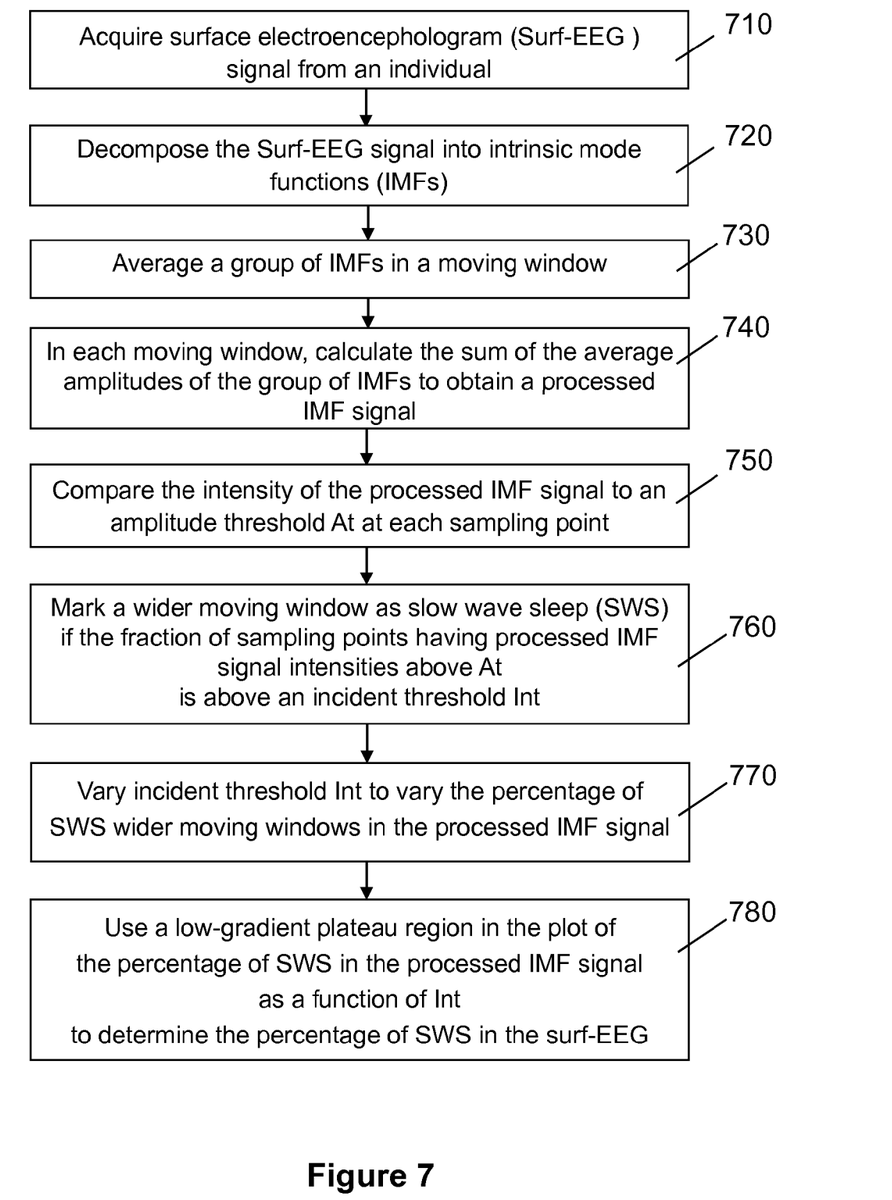
FIG. 7 is an exemplified flow diagram illustrating the steps of quantitatively evaluating sleep in accordance to another aspect of the present invention.
Figure 8:
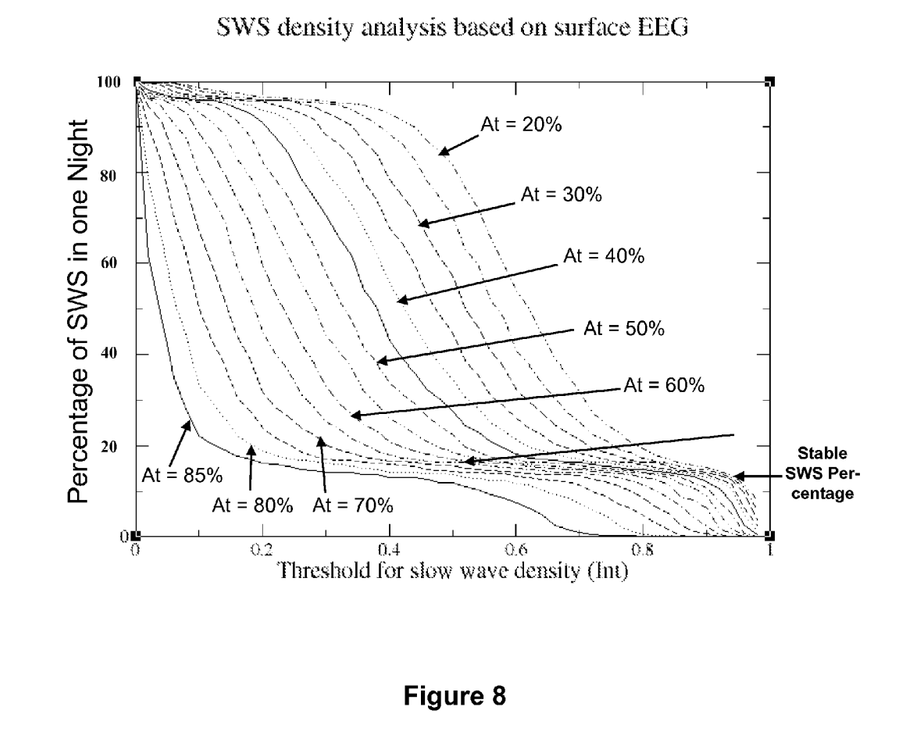
FIG. 8 illustrates the percentages of SWS in a night of an individual's sleep as a function of a threshold for slow wave density (Int) at a family of slow wave amplitude thresholds (At).

In some embodiments, referring to FIGS. 7 and 8, a sleep signal such as surf-EEG is recorded from an individual sleep (step 710). The sleep signal is decomposed into a plurality of intrinsic mode functions (step 720). The waveforms of a group of IMFs such as IMFs 3, 4, 5 can be first averaged with a 2-second moving window at 1-second step size to produce an average amplitude at each second (step 730). The average amplitudes of the IMF 3, 4, 5 are then added to result in a new time series called SW-1 (i.e. the processed IMF signal) (step 740).

The presently disclosed methods define an amplitude threshold (At) for the processed IMF signal (i.e. SW-1 signal). SW-1 signal intensities above At corresponds to a SWS state. Whether the intensity of a SW-1 signal is above At every sampling point (e.g. at 1 second interval) may be impacted by noises in the SW-1 signal. The noises can include common noises as well as discrete SW-like activities in sleep EEG, e.g. K-complex. It is therefore important to distinguish real SWA from noise. To this end, a wider moving window (e.g. 2 minute) is defined. An incidence threshold Int is defined in association with the wider moving window. A SWS state is identified in the wider moving window (2 minute wide) if the fraction of SW-1 intensities (e.g. at 1 second steps) within the wider moving window is above Int. The purpose of At and Int is thus to minimize the impact of noises on the intensities and the frequency occurrences of the SW-1 signal.

Referring to FIG. 8, the percentage of SWS in an individual's one night sleep is plotted against Int for a plurality of At values ranging from 20% to 85% at 5% intervals (for clarity reasons, not all the curves are labeled with respective At values). For a fixed At value such as At =60%, the intensities of the processed IMF signal (e.g. SW-1) at sampling points within each wider window are compared to At to determine if those samplings points satisfy SWS condition (step 750). The wider moving window is determined to be SWS if the fraction of sampling points within that wider moving window is above an Int value (such as Int=0.5) (step 760). The percentage of the wider moving windows that are in SWS state within a night's sleep is plotted against Int in FIG. 7 (step 770).

The curves at different At values in FIG. 7 show that the percentage of SWS are sensitive to the At and Int values. For example, with At =60%, the percentage of SWS decreases as Int increases because fewer wider moving windows are qualified as SWS (more stringent requirement). It was discovered by the present inventors, however, that the At =60% curve has a plateau region at Int above 0.6, wherein the SWS percentage is insensitive to Int and is stabilized at approximately 17%. The plateau region has a low gradient that is lower than a predetermined number such as 0.4 or 0.3. Although the SWS percentage generally decreases as the increase of At values, it was discovered that the curves at different At values (20-85%) all demonstrate similar low gradient plateaus. In accordance to the present invention, the percentage value (e.g. approximately 17%) for the low gradient plateaus can be used as the quantitative SWS percentage to characterize the surf-EEG signal in an individual's sleep (step 780). The low gradient plateaus define "a stable SWS percentage" in the SWS percentage.

In some embodiments, a SWS percentage can be obtained to characterize the surf-EEG signal without varying both At and Int. Referring to FIG. 8, Int can for example be fixed at 0.4. At can be varied to produce a plurality of SWS percentages. It can be seen that the SWS percentage is stabilized at around 17% for At values in the range of 70% to 95%. Similarly, as described above, At can for example be fixed at 70%. The SWS percentage is stabilized at approximately 17% with Int values above 0.5. The stable SWS percentage value can be used to characterize the surf-EEG signal.

An advantage of the above described methods by varying At and/or Int is that there is no requirement for predefined absolute thresholds for IMF signal intensities. The determination of the SWS percentage is based on inherent properties and more basic behavior of the sleep signals. The disclosed method appears to capture the transition point when the intensity of SWA exceeds the intensity of infra-slow oscillations when the network of thalamo-cortical neurons starts to synchronize persistently, giving rise to increasing SWA amplitude, but the arousal related infra-slow oscillations wave in a relatively low level. Moreover, an individual's sleep can be characterized by two states (SWS and active) instead of multiple states, which is especially consistent with observations on NREM (non-rapid eye movements) sleep.

It should be noted that, similar to the steps shown in FIGS. 2 and 3, powers instead of amplitudes can be used in steps 730 to 780.

It should be understood that the above described systems and methods are compatible with different configurations and variations without deviating from the spirit of the present invention. For example, the IMF numbers (3, 4, 5, 8, 9, 10) in the two IMF groups can change as a function of the sampling rate in the data collection. A different set of IMFs (e.g. 4, 5, 6 or 2, 3, 4) can be selected if those IMFs have variation frequencies related to SWS (i.e., deep sleep).

Furthermore, different groups of intrinsic mode functions can be used for quantitatively characterize sleep. For example, IMF 3, IMF 4, IMF 5, IMFs 3-4, IMF 4-5, IMF 2-4 etc. can be used as the low IMF group. IMF 8, IMF 9, IMF 10, IMFs 8-9, IMF 9-10, IMF 7-9 etc. can be used as the high IMF group. The predetermined threshold for the amplitude ratio can have different values from the example (i.e. a value of 1) used above. The moving window can have different temporal durations than 30 seconds. The presently disclosed methods and systems can also be compatible with linear decomposition of the EEG signal to multiple modes.

What is claimed is:

1. A method for quantitative sleep characterization, comprising:
acquiring a surface electroencephalogram (surf-EEG) signal from an individual by a probe;
decomposing the surf-EEG signal into a plurality of intrinsic mode functions (IMFs) by a computer processor in communication with the probe, wherein the plurality of IMFs comprises a first group of IMFs and a second group of IMFs;
calculating a ratio comprising a numerator and denominator, wherein the numerator comprises an amplitude of at least one of the IMFs in the first group, wherein the denominator comprises an amplitude of at least one of the IMFs in the second group; and
identifying a period in the surf-EEG waveform as slow wave sleep (SWS) if the ratio associated with the period is above a first predetermined threshold.

2. The method of claim 1, wherein the step of decomposing the surf-EEG signal is conducted using ensemble empirical mode decomposition.

3. The method of claim 1, wherein the first group of IMFs have characteristic fluctuations in a frequency range from approximately 0.3 Hz to approximately 4 Hz, wherein the second group of IMFs have characteristic fluctuations in a frequency range below approximately 0.3 Hz.

4. The method of claim 3, wherein the second group of IMFs have characteristic fluctuations in a frequency range from approximately 0.01 Hz to approximately 0.2 Hz.

5. The method of claim 1, wherein the first group of IMFs have higher fluctuation frequencies than the second group of IMFs.

6. The method of claim 1, further comprising:
calculating a first average amplitude of at least one of the IMFs in the first group within a moving window to produce a first average amplitude; and
calculating a second average of at least one of the IMFs in the second group within the moving window to produce a second average amplitude, wherein the numerator of the ratio comprises the first average amplitude and the denominator of the ratio comprises the second average amplitude.

7. The method of claim 6, further comprising:
summing the first average amplitudes of the IMFs in the first group within the moving window to produce a first combined average amplitude; and
summing the second average amplitudes of the IMFs in the second group within the moving window to produce a second combined average amplitude, wherein the step of calculating a ratio comprises calculating a ratio of the first combined average amplitude to the second combined average amplitude.

8. The method of claim 6, further comprising:
normalizing the first average amplitude of the at least one of the IMFs in the first group within the moving window to produce a normalized first combined average amplitude; and
normalizing the second average amplitudes of the IMFs in the second group within the moving window to produce a normalized second combined average amplitude, wherein the step of calculating a ratio comprises calculating a ratio of the normalized first combined average amplitude to the normalized second combined average amplitude.

9. The method of claim 6, further comprising:
normalizing the first average amplitudes of the IMFs in the first group within the moving window to produce a normalized first combined average amplitude, wherein a period in the surf-EEG waveform is identified as slow wave sleep (SWS) if the ratio associated with the period is above the first predetermined threshold and the normalized first combined average amplitude is above a second predetermined threshold.

10. A system for quantitative sleep characterization, comprising:
a probe configured to acquire a surface electroencephalogram (surf-EEG) signal from an individual; and
a computer processor in communication with the probe, wherein the computer processor is configured to decompose the surf-EEG signal into a plurality of intrinsic mode functions (IMFs) that comprise a first group of IMFs and a second group of IMFs, to calculate a ratio comprising a numerator and denominator, wherein the numerator comprises an amplitude of at least one of the IMFs in the first group, and wherein the denominator comprises an amplitude of at least one of the IMFs in the second group, wherein the computer processor is configured to identify a period in the surf-EEG waveform as slow wave sleep (SWS) if the ratio associated with the period is above a predetermined threshold.

11. The system of claim 10, wherein the surf-EEG signal is decomposed using ensemble empirical mode decomposition.

12. The system of claim 10, wherein the first group of IMFs have characteristic fluctuations in a frequency range from approximately 0.3 Hz to approximately 4 Hz, wherein the second group of IMFs have characteristic fluctuations in a frequency range below approximately 0.3 Hz.

13. The system of claim 12, wherein the second group of IMFs have characteristic fluctuations in a frequency range from approximately 0.01 Hz to approximately 0.2 Hz.

14. The system of claim 10, wherein the first group of IMFs have higher fluctuation frequencies than the second group of IMFs.

15. The system of claim 10, wherein the computer processor is configured to
calculate a first average amplitude of at least one of the IMFs in the first group within a moving window to produce a first average amplitude; and
calculate a second average of at least one of the IMFs in the second group within the moving window to produce a second average amplitude, wherein the numerator of the ratio comprises the first average amplitude and the denominator of the ratio comprises the second average amplitude.

16. The system of claim 15, wherein the computer processor is configured to
sum the first average amplitudes of the IMFs in the first group within the moving window to produce a first combined average amplitude; and
sum the second average amplitudes of the IMFs in the second group within the moving window to produce a second combined average amplitude, wherein the step of calculating a ratio comprises calculating a ratio of the first combined average amplitude to the second combined average amplitude.

17. The system of claim 15, wherein the computer processor is configured to
normalize the first average amplitude of the at least one of the IMFs in the first group within the moving window to produce a normalized first combined average amplitude; and
normalize the second average amplitudes of the IMFs in the second group within the moving window to produce a normalized second combined average amplitude, wherein the step of calculating a ratio comprises calculating a ratio of the normalized first combined average amplitude to the normalized second combined average amplitude.

18. The system of claim 15, wherein the computer processor is configured to
normalize the first average amplitudes of the IMFs in the first group within the moving window to produce a normalized first combined average amplitude, within a period in the surf-EEG waveform is identified as slow wave sleep (SWS) if the ratio associated with the period is above the first predetermined threshold and the normalized first combined average amplitude is above a second predetermined threshold.

19. A method for quantitative sleep characterization, comprising:
acquiring a surface electroencephalogram (surf-EEG) signal from an individual by a probe;
decomposing the surf-EEG signal into a plurality of intrinsic mode functions (IMFs) by a computer processor in communication with the probe, wherein the plurality of IMFs comprises a first group of IMFs and a second group of IMFs;
calculating a first average amplitude of at least one of the IMFs in the first group within a moving window to produce a first average amplitude;
calculating a second average of at least one of the IMFs in the second group within the moving window to produce a second average amplitude;
summing the first average amplitudes of the IMFs in the first group within the moving window to produce a first combined average amplitude;
summing the second average amplitudes of the IMFs in the second group within the moving window to produce a second combined average amplitude
calculating a ratio comprising a numerator and denominator, wherein the numerator comprises the first combined average amplitude, wherein the denominator comprises the second combined average amplitude; and
identifying a period in the surf-EEG waveform as slow wave sleep (SWS) if the ratio associated with the period is above a first predetermined threshold.

20. A method for quantitative sleep characterization, comprising:
acquiring a surface electroencephalogram (surf-EEG) signal from an individual by a probe;
decomposing the surf-EEG signal into a plurality of intrinsic mode functions (IMFs) by a computer processor in communication with the probe, wherein the plurality of IMFs comprises a first group of IMFs and a second group of IMFs;
calculating a first average amplitude of at least one of the IMFs in the first group within a moving window to produce a first average amplitude;
calculating a second average of at least one of the IMFs in the second group within the moving window to produce a second average amplitude;
calculating a ratio comprising a numerator and a denominator, wherein the numerator of the ratio comprises the first average amplitude, wherein the denominator of the ratio comprises the second average amplitude;
normalizing the first average amplitudes of the IMFs in the first group within the moving window to produce a normalized first combined average amplitude;
identifying a period in the surf-EEG waveform as slow wave sleep (SWS) if the ratio associated with the period is above a first predetermined threshold and the normalized first combined average amplitude is above a second predetermined threshold.

* * * * *